United States Patent [19]

Amschler

[11] 4,277,472

[45] Jul. 7, 1981

[54] 3,6-DISUBSTITUTED-5,7-(LOWER ALKANO)-5,6,7,8-TETRAHYDROPYRIDO(4,3-C)PYRIDAZINES; THEIR INTERMEDIATES, PREPARATION, ANTIHYPERTENSIVE USE AND COMPOSITIONS

[75] Inventor: Hermann Amschler, Radolfzell, Fed. Rep. of Germany

[73] Assignee: Byk Gulden Lomberg Chemische Fabrik GmbH, Konstanz, Fed. Rep. of Germany

[21] Appl. No.: 88,469

[22] Filed: Oct. 26, 1979

[30] Foreign Application Priority Data

Nov. 10, 1978 [CH] Switzerland ........................ 11585/78

[51] Int. Cl.³ .................. C07D 451/14; C07D 471/18; A61K 31/50

[52] U.S. Cl. ................................ 424/248.5; 544/234; 546/183; 546/124; 546/112; 424/248.52; 424/248.54; 424/250

[58] Field of Search ................ 544/234, 115; 424/250, 424/248.5, 248.52, 248.54

[56] References Cited

U.S. PATENT DOCUMENTS

| | | | |
|---|---|---|---|
| 3,838,125 | 9/1974 | Sandoz | 544/234 |
| 3,954,754 | 4/1976 | Sandoz | 544/234 |
| 4,179,506 | 12/1979 | Butler | 424/256 |
| 4,179,524 | 12/1979 | Grivsky | 424/324 |
| 4,181,737 | 1/1980 | Wagner et al. | 424/319 |

FOREIGN PATENT DOCUMENTS 1475590 1/1977 United Kingdom .

OTHER PUBLICATIONS

Landa, Chem. Abs. 83, 178965.

*Primary Examiner*—Mark L. Berch

*Attorney, Agent, or Firm*—Berman, Aisenberg & Platt

[57] ABSTRACT

Substituted pyridazines of formula I

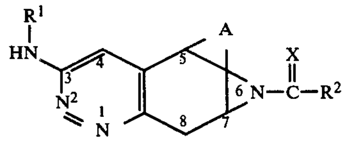

(I), wherein

A denotes a lower alkylene group, $R^1$ denotes an optionally-substituted or derivatized amino group, $R^2$ denotes an alkyl group, an alkoxy group, an alkylmercapto group, an optionally-substituted aryl group, a phenalkoxy group or an optionally-substituted amino group and X denotes an oxygen atom or a sulfur atom, and their acid-addition salts with inorganic and organic acids are new compounds. They have an anti-hypertensive effect and are suitable for the treatment of hypertension. Processes for the preparation of the new, pharmacologically-effective compounds, new intermediate products required for their preparation, therapeutic use of the compounds, compositions for such use and unit dosage forms of the compositions are disclosed.

29 Claims, No Drawings

3,6-DISUBSTITUTED-5,7-(LOWER ALKANO)-5,6,7,8-TETRAHYDROPYRIDO(4,3-C)PYRIDAZINES; THEIR INTERMEDIATES, PREPARATION, ANTIHYPERTENSIVE USE AND COMPOSITIONS

THE TECHNICAL FIELD

The invention relates to medicament compositions, to their uses as anti-hypertensives, to their production and to intermediate products (including an essential active ingredient upon which the compositions are based) for their preparation.

BACKGROUND ART 1-hydrazinophthalazine (hydralazine), its anti-hypertensive effectiveness and its side-effects are known (Ehrhard/Ruschig: Arzneimittel, 2nd Edition, Volume 2, pages 278/79, Verlag Chemie, Weinheim/Bergstrasse, 1972). Anti-hypertensive properties are also ascribed to hydralazine derivatives described in U.S. Pat. No. 3,838,125, U.S. Pat. No. 3,954,754 and in British Patent Specification No. 1,475,590.

STATEMENT OF THE INVENTION

The invention is based upon substituted pyridazines of formula H,

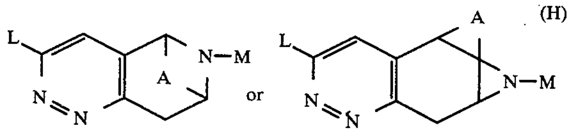

or (H)

wherein

A denotes a lower alkylene group,

L denotes a leaving group Z or a —NH—$R^1$ group,

M denotes a hydrogen atom (—H) or a —C(=X)$R^2$ group, $R^1$ denotes an optionally-substituted or derivatized amino group, $R^2$ denotes an alkyl group, a phenalkyl group, an alkoxy group, an alkylmercapto group, an optionally-substituted aryl group, a phenalkoxy group or an optionally-substituted amino group and X denotes an oxygen atom or a sulfur atom, and their acid-addition salts with inorganic or organic acids.

Although the invention is primarily directed to pharmacologically-active and physiologically-acceptable substituted pyridazines, it has a number of additional aspects which are all intimately related thereto and which combine together to form a single unit. These various aspects are:

(a) pharmacologically-active and physiologically-acceptable substituted pyridazines [compounds of formula H wherein L is —NH—$R^1$ and M is —C(=X)$R^2$] and physiologically-acceptable acid-addition salts thereof, (b) synthesis of (a), (c) novel [all compounds of formula H other than those wherein L is —NH—$R^1$ and M is, concurrently, —C(=X)$R^2$] substituted-pyridazine and acid-addition-salt intermediates in (b), (d) therapeutic use of (a), (e) compositions administered in (d) and (f) dosage forms of (e).

The pharmacologically-active and physiologically-acceptable substituted pyridazines have a significantly-higher therapeutic effectiveness for reducing blood pressure than hydralazine and other compounds which (structurally) are even more closely related.

DEFINITION OF TERMS

Throughout the specification and claims a number of words and expressions appear repeatedly. Some of these are presented for ease of reference. Each of the following has its stated meaning throughout the entire text in the absence of another specified definition at a particular occurrence.

acid-binding agent—a proton acceptor, e.g. an alkali-metal carbonate, such as sodium carbonate or potassium carbonate, or a tertiary organic amine, such as triethylamine, N,N-diisopropylethylamine and N,N-dicyclohexylethylamine.

alkane carboxylic acid —R—CO—OH, where R is straight-chain or branched alkyl with, e.g., from 1 to 7 carbon atoms, preferably lower alkyl with from 1 to 5 carbon atoms (e.g. acetic acid, propionic acid and isobutyric acid).

alkanoyl—a radical, R—CO—, (e.g. acetyl, propionyl and butyryl) derived from an alkane carboxylic acid, as hereinbefore defined.

alkenyl—olefinically unsaturated hydrocarbyl (e.g. allyl, 2-butenyl and 2-pentenyl) having, e.g., one double bond and from 3 to 7, preferably from 3 to 5, carbon atoms.

alkoxy—a radical, R—O—, (e.g. methoxy, isopropoxy and amyloxy) where R is straight-chain or branched alkyl with from 1 to 7 carbon atoms, preferably lower alkyl with from 1 to 5 carbon atoms.

alkoxycarbonyl—a radical, R—O—CO—, (e.g. methoxycarbonyl, isopropoxycarbonyl and butoxycarbonyl) where R is straight-chain or branched alkyl with from 1 to 7 carbon atoms, preferably lower alkyl with from 1 to 5 carbon atoms.

alkyl—straight-chain or branched saturated hydrocarbyl, e.g. those having from 1 to 7 carbon atoms, such as methyl, ethyl, propyl, isopropyl, butyl, isobutyl, sec.-butyl, tert.-butyl, pentyl, hexyl and heptyl. Lower alkyl with from 1 to 5, especially those with 1 or 2, carbon atoms are preferred. Of the branched alkyl those having from 3 to 5, especially 4, carbon atoms are preferred.

alkylene—a linear or branched divalent saturated aliphatic hydrocarbon, e.g. lower alkylene having from 1 to 5, preferably 2 or 3, carbon atoms, such as methylene, ethylene, propylene and 2,2-dimethylpropylene.

alkylmercapto—a radical, R—S—, (e.g. methylmercapto, isopropylmercapto and butylmercapto) where R is straight-chain or branched alkyl with from 1 to 7 carbon atoms, preferably lower alkyl with from 1 to 5 carbon atoms.

aryl—carbocyclic aromatic hydrocarbyl having from 6 to 10 ring carbon atoms, e.g. phenyl, α-naphthyl and β-naphthyl, preferably phenyl.

chiral—compounds which contain at least one asymmetric carbon atom; as a result two molecule forms, the one being the mirror image of the other (enantiomers), are possible.

derivatized amino—a radical, —N=C($R^8$)$R^9$, where $R^8$ is a hydrogen atom (—H), lower alkyl, phenalkyl, aryl or substituted aryl; $R^9$ is lower alkyl, phenalkyl, lower alkenyl, aryl or substituted aryl; or $R^8$ and $R^9$ together, represent linear alkylene with from 4 to 11, preferably from 5 to 7, carbon atoms, e.g. pentamethylene and hexamethylene.

(di)alkylcarbamoyl —NHRCO— or $NR_2CO$— (e.g. dimethylcarbamoyl or ethylcarbamoyl) where R has the meaning of alkyl as hereinbefore defined.

halo—chloro, bromo, fluoro or iodo.

halogen atom—c.f. halo.

heterocycle—a five- to eight-, preferably five- or six-membered nitrogen-containing ring having at most one other ring hetero atom (nitrogen, oxygen or sulfur), e.g. pyrrolidine, piperidine, morpholine, thiomorpholine and piperazine.

heterocyclic group—a ring-nitrogen-containing heterocyclic radical wherein a ring nitrogen has a free valence bond and the heterocycle is as hereinbefore defined, e.g. pyrrolidino, piperidino, morpholino, thiomorpholino, piperazino, oxazolidino, thiazolidino and imidazolidino.

individual dose—A medicament dose which preferably contains the amount of active substance which is administered in one application and which usually corresponds to a whole, a half, a third or a quarter of the daily dose.

leaving group—an easily replaceable group, e.g. alkoxy, such as methoxy or ethoxy; mercapto; alkylmercapto, such as methylmercapto; alkylsulfinyl, such as methylsulfinyl, alkylsulfonyl, such as ethylsulfonyl; or, preferably, halo, especially bromo or chloro.

lower—(when modifying an aliphatic group, e.g. alkyl, alkylene, alkoxy or alkylmercapto) a group having from 1 to 7 (preferably from 1 to 5) carbon atoms, inclusive.

optionally—with or without; often used with "substituted" and a stated group to indicate that the stated group is either unsubstituted or substituted.

phenalkyl—phenylalkylene wherein the alkylene is preferably unbranched and preferably contains from 1 to 4 carbon atoms, e.g. benzyl and phenethyl.

proton acceptor—an acid binding agent.

salt—acid-addition salt; preferably, but not necessarily, a pharmacologically-compatible acid-addition salt of an organic or inorganic acid conventionally employed in galenical medicine. Pharmacologically-incompatible salts (as long as they are soluble in some solvent) are readily and conventionally converted into pharmacologically-compatible salts; both are conventionally converted into corresponding free bases. Suitable acid-addition salts are either water-soluble or water-insoluble salts, e.g. the hydrochloride, hydrobromide, hydriodide, phosphate, nitrate, sulfate, acetate, citrate, gluconate, benzoate, hibenzate [2-(4-hydroxybenzoyl)benzoate], fendizoate o-[2'-hydroxy-4-biphenylyl)carbonyl]benzoate, propionate, butyrate, sulfosalicylate, maleate, laurate, malate, fumarate, succinate, oxalate, tartrate, amsonate (4,4'-diaminostilbene-2,2'-disulfonate), embonate (1,1'-methylene-bis-2-hydroxy-3-naphthoate), metembonate, stearate, tosylate (p-toluenesulfonate), 2-hydroxy-3-naphthoate, 3-hydroxy-2-naphthoate, mesylate (methanesulfonate); further, salts with bumetanide [3-(butylamino)-4-phenoxy-5-sulfamoylbenzoic acid], furosemide (4-chloro-N-furfuryl-5-sulfamoylanthranilic acid), azosemide [5-(4-chloro-5-sulfamoyl-2-thenylamino)phenyltetrazol], galosemide [N-{[4-(α,α,α-trifluoro-m-toluidino)-3-pyridyl]sulfonyl}propionamide], besunide [4-benzyl-3-(butylamino)-5-sulfamoylbenzoic acid], piretanide [4-phenoxy-3-(1-pyrrolidinyl)-5-sulfoamoylbenzoic acid], ethacrynic acid {[2,3-dichloro-4-(2-methylenebutyryl)phenoxy]acetic acid}, thienilic acid {[2,3-dichloro-4-(2-thenoyl)phenoxy]-acetic acid}, 4-chloro-3-sulflamoylbenzoic acid.

substituted amino—amino (—$NH_2$) with either (e.g. —NH—$R^3$) or both [e.g. —N($R^4$)$R^5$] of the hydrogen atoms replaced by the same or different radicals. Substituted amino $R^1$ can be —NH—$R^3$ or —N($R^4$)$R^5$; when $R^3$ is other than a hydrogen atom (—H), it is alkanoyl (e.g. acetyl), alkoxycarbonyl (e.g. ethoxycarbonyl) or (di)alkylcarbamoyl (e.g. dimethylcarbamoyl); each of $R^4$ and $R^5$ is, independently, lower alkyl (e.g. propyl) or phenalkyl (e.g. benzyl). Substituted amino $R^2$ is characterized by —N($R^6$)$R^7$, wherein each of $R^6$ and $R^7$ is, independently, a hydrogen atom (—H), alkyl (e.g. methyl), phenalkyl (e.g. phenethyl), optionally-substituted aryl (e.g. phenyl) or, together with the nitrogen atom to which both are bound, an optionally-substituted heterocyclic radical, i.e. $R^6$ and $R^7$ taken together are polymethylene with from 4 to 7 methylene groups or such polymethylene with one methylene replaced by a member selected from the group consisting of —O—, —S—, —NH— or —N(lower alkyl)—(e.g. pyrrolidino and 4-methylpiperazino).

substituted aryl—aryl substituted in any and every desired position (not barred, e.g., by steric hindrance), for example with 2 substituents, preferably with 1 substituent; the energetically-favored positions are preferred. Substituents include, but are not limited to, halogen atoms, for example fluorine and bromine, preferably chlorine; alkyl, alkoxy or alkylmercapto groups with, in each case, from 1 to 4 carbon atoms in the alkyl moiety; the trifluoromethyl group or the nitro group. Examples of substituted aryl groups are o-chlorophenyl, m-chlorophenyl, p-chlorophenyl, m-bromophenyl, p-bromophenyl, p-fluorophenyl, m-tolyl, p-tolyl, 3,4-dichlorophenyl, 3-chloro-p-tolyl, α,α,α-trifluoro-m-tolyl, p-nitrophenyl, m-nitrophenyl, p-methoxyphenyl, p-ethoxyphenyl, 3,4-dimethoxyphenyl, cumenyl, p-butylmercaptophenyl and 4-chloro-1-naphthyl, of which halo-substituted phenyl groups are preferred.

substituted heterocyclic group—a heterocyclic group with two ring nitrogen atoms, one of which is substituted by lower alkyl or benzyl, e.g. 4-methylpiperazino.

transient group—leaving group.

unit dose—a tablet, a dragée, a capsule, a suppository or a measured volume amount of a powder, granulate, solution, emulsion or suspension; a physically-determined unit which contains an individual amount of the active constituent in combination with a pharmaceutical excipient and whose active-substance content corresponds to a fraction or multiple of a therapeutic individual dose. When, for an individual therapeutic administration, only a fraction, such as a half or a quarter, of the unit dose is needed, the unit dose is advantageously divisible, e.g., in the form of a tablet with a break score.

DETAILS

The compounds of the invention are primarily substituted 5,7-(lower alkano)-5,6,7,8-tetrahydropyrido-[4,3-c]pyridazines of formula (H) wherein A is lower alkylene, L is —NH—$R^1$ or Z, M is —H or —C(=X)$R^2$, $R^1$ is optionally-substituted amino or derivatized amino, $R^2$ is lower alkyl, phen(lower)alkyl, lower alkoxy, lower alkylmercapto, optionally-substituted (aryl having from 6 to 10 ring-carbon atoms), phen(lower-)alkoxy or optionally-substituted amino, X is an oxygen atom or a sulfur atom, and Z is a leaving group, or an acid-addition salt thereof;

any substituent of substituted amino $R^1$ being, e.g. lower alkanoyl, lower alkoxycarbonyl, (di)alkylcarbamoyl; of substituted amino $R^2$ being lower alkyl, phen(lower)alkyl, optionally-substituted (aryl having from 6 to 10 ring-carbon atoms) or, two substituents taken together, tetramethylene, pentamethylene or either with one methylene replaced by a member selected from the group consisting of —O—, —S—, —NH— or —N(lower alkyl)—;

any substituent of substituted aryl being, e.g., halo, lower alkyl, lower alkoxy, lower alkylmercapto, trifluoromethyl or nitro.

One aspect of the invention concerns pyridazines of formula I

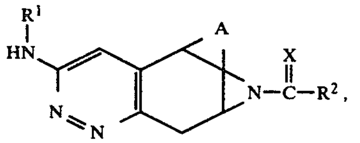
(I)

wherein

A is lower alkylene, $R^1$ is optionally-substituted or derivatized amino, $R^2$ is lower alkyl, phen(lower)alkyl, lower alkoxy, lower alkylmercapto, optionally-substituted aryl (having from 6 to 10 ring-carbon atoms), phen(lower-)alkoxy or optionally-substituted amino and X is an oxygen atom or a sulfur atom, and their acid-addition salts.

One embodiment of such compounds (Ia) concerns pyridazines of formula I wherein

A denotes an alkylene radical with 2 or 3 carbon atoms, $R^1$ denotes $—NH—R^3$ or $—N{=}C(R^8)R^9$, $R^2$ denotes lower alkyl, phenalkyl, lower alkoxy, optionally-substituted phenyl or $—N(R^6)R^7$, $R^3$ denotes a hydrogen atom (—H), lower alkanoyl or lower alkoxycarbonyl, $R^6$ denotes a hydrogen atom (—H), lower alkyl or phenalkyl, $R^7$ denotes lower alkyl, phenalkyl or optionally-substituted phenyl or $R^6$ and $R^7$, together with the nitrogen atom to which both are bound, represent piperidino, morpholino, piperazino or 4-(lower alkyl)-piperazino, $R^8$ denotes lower alkyl, phenalkyl or optionally-substituted phenyl, $R^9$ denotes lower alkyl, phenalkyl or optionally-substituted phenyl and X denotes an oxygen atom, and their acid-addition salts.

A further embodiment of such compounds (Ib) involves pyridazines of formula I wherein A denotes an alkylene radical with 2 to 3 carbon atoms, $R^1$ denotes $—NH—R^3$ or $—N{=}C(R^8)R^9$, $R^2$ denotes lower alkyl, phenalkyl, lower alkoxy, phenyl or $—N(R^6)R^7$, $R^3$ denotes a hydrogen atom (—H) or lower alkoxycarbonyl, $R^6$ denotes a hydrogen atom (—H)

$R^7$ denotes lower alkyl, phenalkyl or phenyl, $R^8$ denotes lower alkyl or phenalkyl, $R^9$ denotes lower alkyl, phenalkyl or optionally-monohalosubstituted phenyl and X denotes an oxygen atom, and their acid-addition salts.

Preferred representatives of embodiment (Ib) are those (Ic) in which $R^2$ denotes tert.-butyl, ethoxy, phenyl or $—N(R^6)R^7$, $R^3$ denotes a hydrogen atom (—H) or ethoxycarbonyl, $R^7$ denotes methyl, $R^8$ denotes methyl, $R^9$ denotes methyl, ethyl or p-chlorophenyl and X represents an oxygen atom, and their pharmacologically-compatible acid-addition salts with inorganic or organic acids.

Particularly preferred representatives of this embodiment (Ic) are those (Id) in which $R^2$ denotes an ethoxy or a phenyl group, $R^3$ denotes a hydrogen atom (—H), $R^8$ denotes methyl, $R^9$ denotes methyl and X represents an oxygen atom, and their pharmacologically-compatible acid-addition salts with inorganic or organic acids.

In addition to compounds of formula I and the noted embodiments (Ia, Ib, Ic and Id) thereof, this invention includes corresponding compounds of each of the formulae:

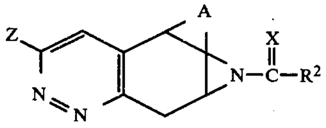
(II)

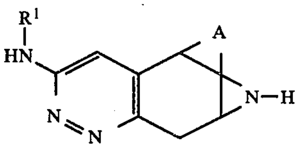
(II')

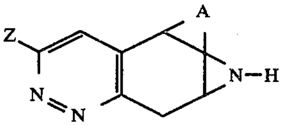
(VI)

wherein each of A, $R^1$, $R^2$, X and Z has its previously-ascribed meaning. It also includes corresponding embodiments (IIa, IIb, IIc, IId, II'a, II'b, II'c, II'd, VIa, VIb, VIc and VId) with the more-limited meanings of the respective variables.

In the group of embodiments consisting of IIa, II'a and VIa

A denotes an alkylene radical with 2 or 3 carbon atoms, $R^1$ denotes $—NH—R^3$ or $—N{=}C(R^8)R^9$, $R^2$ denotes a lower alkyl, phenalkyl, lower alkoxy, optionally-substituted phenyl or $—N(R^6)R^7$, $R^3$ denotes a hydrogen atom (—H), lower alkanoyl or lower alkoxycarbonyl, $R^6$ denotes a hydrogen atom (—H), lower alkyl or phenalkyl, $R^7$ denotes lower alkyl, phenalkyl or optionally-substituted phenyl or $R^6$ and $R^7$, together with the nitrogen atom to which both are bound, represent piperidino, morpholino, piperazino or 4-(lower alkyl)piperazino, $R^8$ denotes lower alkyl, phenalkyl or optionally-substituted phenyl, $R^9$ denotes lower alkyl, phenalkyl or optionally-substituted phenyl, X denotes an oxygen atom, and Z denotes a halogen atom.

In the group of embodiments consisting of IIb, II'b and VIb

A denotes an alkylene radical with 2 to 3 carbon atoms, $R^1$ denotes —NH—$R^3$ or —N=C($R^8$)$R^9$, $R^2$ denotes lower alkyl, phenalkyl, lower alkoxy, phenol or —N($R^6$)$R^7$, $R^3$ denotes a hydrogen atom (—H) or lower alkoxycarbonyl, $R^6$ denotes a hydrogen atom (—H)

$R^7$ denotes lower alkyl, phenalkyl or phenyl, $R^8$ denotes lower alkyl or phenalkyl, $R^9$ denotes lower alkyl, phenalkyl or optionally-monohalo-substituted phenyl, X denotes an oxygen atom and Z denotes a bromine or a chlorine atom.

All groups of compounds of formulae II' and VI include corresponding acid-addition salts.

The compounds according to the invention are chiral molecules. The invention thus includes both the enantiomers and their mixtures and racemates.

Representative compounds of the invention include:

3-hydrazino-5,7-propano-5,6,7,8-tetrahydro-6-pyrido[4,3-c]-pyridazine carboxylic acid benzyl ester,
3-hydrazino-5,7-propano-5,6,7,8-tetrahydro-6-pyrido[4,3-c]-pyridazine carboxylic acid tert.-butyl ester,
3-hydrazino-5,7-propano-5,6,7,8-tetrahydro-6-pyrido[4,3-c]-pyridazine carboxylic acid pentyl ester,
3-(1,3-dimethyl-2-butenylidenehydrazino)-5,7-propano-5,6,7,8-tetrahydro-6-pyrido[4,3-c]pyridazine carboxylic acid tert.-butyl ester,
3-cyclopentylidenehydrazino-5,7-propano-5,6,7,8-tetrahydro-6-pyrido[4,3-c]pyridazine carboxylic acid benzyl ester,
3-(2-ethoxycarbonylhydrazino)-5,7-propano-5,6,7,8-tetrahydro-6-pyrido[4,3-c]pyridazine carboxylic acid N-methyl amide,
3-(4-methyl-semicarbazido)-5,7-propano-5,6,7,8-tetrahydro-6-pyrido[4,3-c]pyridazine carboxylic acid N,N-dimethyl amide,
3-(2-acetylhydrazino)-5,7-propano-5,6,7,8-tetrahydro-6-pyrido[4,3-c]pyridazine thiocarboxylic acid ethyl ester,
3-(1-phenylethylidenehydrazino)-5,7-propano-5,6,7,8-tetrahydro-6-pyrido[4,3-c]pyridazine carboxylic acid N-methyl amide,
3-hydrazino-6-phenacetyl-5,7-propano-5,6,7,8-tetrahydropyrido-[4,3-c]pyridazine,
6-butyryl-3-hydrazino-5,7-propano-5,6,7,8-tetrahydropyrido-[4,3-c]pyridazine,
3-butylidenehydrazino-6-propionyl-5,7-propano-5,6,7,8-tetrahydropyrido[4,3-c]pyridazine,
3-(1,3-dimethyl-2-butenylidenehydrazino)-6-(3,4-dichlorobenzoyl)-5,7-propano-5,6,7,8-tetrahydropyrido[4,3-c]pyridazine,
3-hydrazino-6-(p-toluoyl)-5,7-propano-5,6,7,8-tetrahydropyrido[4,3-c]pyridazine,
6-(4-chlorobenzoyl)-3-(2-methoxycarbonylhydrazino)-5,7-propano-5,6,7,8-tetrahydropyrido[4,3-c]pyridazine,
3-hydrazino-6-pivaloyl-5,7-ethano-5,6,7,8-tetrahydropyrido-[4,3-c]pyridazine,
6-(2-chlorobenzoyl)-3-hydrazino-5,7-ethano-5,6,7,8-tetrahydropyrido[4,3-c]pyridazine,
3-hydrazino-5,7-ethano-5,6,7,8-tetrahydro-6-pyrido[4,3-c]-pyridazine carboxylic acid amide,
3-hydrazino-5,7-ethano-5,6,7,8-tetrahydro-6-pyrido[4,3-c]-pyridazine carboxylic acid tert.-butyl ester,
3-cyclohexylidenehydrazino-5,7-ethano-5,6,7,8-tetrahydro-6-pyrido[4,3-c]pyridazine carboxylic acid ethyl ester,
3-bromo-5,7-propano-5,6,7,8-tetrahydro-6-pyrido[4,3-c]-pyridazine carboxylic acid ethyl ester,
3-chloro-5,7-propano-5,6,7,8-tetrahydro-6-pyrido[4,3-c]-pyridazine carboxylic acid-N,N-dimethylamide,
3-chloro-6-(4-chlorobenzoyl)-5,7-propano-5,6,7,8-tetrahydropyrido[4,3-c]pyridazine,
3-hydrazino-5,7-ethano-5,6,7,8-tetrahydropyrido[4,3-c]-pyridazine,
3-(2-methoxycarbonylhydrazino)-5,7-propano-5,6,7,8-tetrahydropyrido[4,3-c]pyridazine,
3-[1-(p-chloro)phenylethylidenehydrazino]-5,7-propano-5,6,7,8-tetrahydropyrido[4,3-c]pyridazine, and their acid-addition salts.

Preferred representatives are:

6-benzoyl-3-isopropylidenehydrazino-5,7-propano-5,6,7,8-tetrahydropyrido[4,3-c]pyridazine,
3-isopropylidenehydrazino-5,7-ethano-5,6,7,8-tetrahydro-6-pyrido[4,3-c]pyridazine carboxylic acid ethyl ester
3-chloro-5,7-propano-5,6,7,8-tetrahydro-6-pyrido[4,3-c]-pyridazine carboxylic acid ethyl ester,
3-chloro-5,7-ethano-5,6,7,8-tetrahydro-6-pyrido[4,3-c]-pyridazine carboxylic acid ethyl ester,
6-benzoyl-3-chloro-5,7-propano-5,6,7,8-tetrahydropyrido[4,3-c]pyridazine,
3-chloro-6-pivaloyl-5,7-propano-5,6,7,8-tetrahydropyrido-[4,3-c]pyridazine,
3-chloro-5,7-propano-5,6,7,8-tetrahydro-6-pyrido[4,3-c]-pyridazine carboxylic acid N-methyl amide,
3-isopropylidenehydrazino-5,7-propano-5,6,7,8-tetrahydropyrido[4,3-c]pyridazine,
3-chloro-5,7-propano-5,6,7,8-tetrahydropyrido[4,3-c]-pyridazine and, in particular,
3-hydrazino-5,7-propano-5,6,7,8-tetrahydro-6-pyrido[4,3-c]pyridazine carboxylic acid ethyl ester, and their acid-addition salts.

The compounds according to the invention possess valuable properties which make them commercially useful. The substituted pyridazines of formula I, their preferred representatives (including embodiments Ia, Ib, Ic and Id) and their acid-addition salts are pharmacologically-effective compounds according to the invention; in particular, they lower blood pressure. This is confirmed by investigations on awake, genetically-hypertensive rats. The pharmacologically-effective compounds according to the invention, e.g. 3-hydrazino-5,7-propano-5,6,7,8-tetrahydro-6-pyrido[4,3-c]pyridazine carboxylic acid ethyl ester, have a considerably higher anti-hypertensive effectiveness and longer duration of action than hydralazine or compounds of U.S. Pat. No. 3,838,125, U.S. Pat. No. 3,954,754 or of British Patent Specification No. 1,475,590. Furthermore, compared with the state of the art, they are characterized by better tolerance, as determinations of the $LD_{50}$ after a single oral administration to the mouse (in comparison with hydralazine) showed. In view of the properties, in particular the increased effectiveness and longer duration of action, the pharmacologically-effective compounds according to the invention represent a therapeutic advance and a desired enrichment of the state of the art. The substituted pyridazines according to the invention of formulae II, II', and VI are valuable intermediates for the production of the pharmacologically-effective compounds of the invention.

The excellent effectiveness of the pharmacologically-effective compounds according to the invention permits their use in human medicine; the indications are, in particular, primary and secondary hypertension of all degrees of severity.

The invention thus further relates to a process for the treatment of mammals suffering from one or more of the previously-mentioned diseases. The process is characterized by administering a therapeutically-active and pharmacologically-tolerated amount of one or more physiologically-acceptable compounds of formula I or their preferred representatives and/or their pharmaceutically-acceptable salts to a sick mammal. The invention also relates to the use of compounds according to the invention in combating the previously-noted illnesses. The invention likewise comprises the use of the compounds according to the invention for the preparation of medicaments which are employed for combating the listed illnesses.

A further aspect of the invention therefore comprises medicaments which contain one or more substituted pyridazines of formula I and/or their pharmacologically-compatible acid-addition salts with inorganic or organic acids.

The medicaments are prepared according to processes known per se; the new compounds are used as such or, where appropriate, in combination with suitable pharmaceutical excipients. When the new pharmaceutical preparations contain, besides the active substances, pharmaceutical excipients, the active-substance content of these mixtures is from 0.1 to 99.5, preferably from 0.5 to 95, percent by weight of the total mixture.

In accord with the invention the active substances are applied in any suitable formulation, with the proviso that the formation or maintenance of sufficient blood levels is ensured. That can be achieved, for example, through oral or parenteral administration in suitable doses. Advantageously, the pharmaceutical preparation of the active substance is present in the form of unit doses which are matched to the desired administration.

The pharmaceutical preparations according to the invention contain, when they are present in unit doses and are intended for administration, e.g., to humans, from about 0.1 to 500 mg, advantageously from 0.5 to 100 mg and, in particular, from 1 to 30 mg, of active substance.

In general it has, in human medicine, proved advantageous, in order to achieve the desired results, to administer the active substance(s), in oral administration, in a daily dose of from about 0.001 to about 5, preferably from 0.01 to 2, in particular from 0.05 to 1, mg/kg of body weight, in the form (where appropriate) of several, preferably from 1 to 3, individual administrations. An individual administration contains the active substance(s) in amounts of from about 0.001 to about 2.5, preferably from 0.01 to 1.5, in particular from 0.05 to 0.5, mg/kg of body weight. In parenteral, e.g. intravenous, treatment similar dosages are applied.

The therapeutic administration of the pharmaceutical preparation is effected from 1 to 4 times daily at fixed or varying points in time, e.g. after each meal and/or in the evening. It may, however, be necessary to deviate from such dosages, depending on the nature, the body weight and the age of the individual to be treated, the nature and the severity of the disease, the nature of the preparation and the application of the medicament as well as the space in time or interval within which the administration is effected. Thus, in some cases it suffices to manage with less than the previously-mentioned amount of active substance, whereas in other cases the previously-mentioned amount of active substance must be exceeded. In the case of low initial dose, a low dose is administered at the beginning of the treatment; a slow transition to a higher dose is then made. After achievement of the desired lowering of blood pressure, a lower dose is then reverted to.

The fixing of an optimum dose, and duration, frequency and type of administration of the active substance is readily effected on the basis of the specialized knowledge of anyone skilled in the art.

The pharmaceutical preparations consist, as a rule, of the active substance according to the invention and non-toxic, pharmaceutically-compatible medicament excipients which are used in admixture or as diluent in solid, semi-solid or liquid form or as a surrounding agent, for example in the form of a capsule, a tablet coating, a bag or other container, for the therapeutically-active constituent. An excipient serves, e.g., as agent for the absorption of the medicament by the body, as formulation auxiliary, as sweetener, as taste corrector, as dyestuff or as preservative.

For oral application tablets, dragees, hard and soft capsules, e.g. of gelatin, dispersible powders, granulates, aqueous and oily suspensions, emulsions, solutions or syrups are useful.

Tablets may contain inert diluents, e.g. calcium carbonate, calcium phosphate, sodium phosphate or lactose; granulation and distribution agents, e.g. maize starch or alginates; binders, e.g. starch, gelatin or acacia gum; and lubricant, e.g. aluminum stearate or magnesium stearate, talc or silicone oil. They are, optionally, additionally provided with a coating which is, e.g., of such a nature that it causes a delayed dissolving and absorption of the medicament in the gastro-intestinal tract, so that a better tolerance, protraction or retardation is achieved. Gelatin capsules optionally contain the medicament mixed with a solid diluent, e.g. calcium carbonate or kaolin, or an oily diluent, e.g. olive, arachis or paraffin oil.

Aqueous suspensions contain, for example, suspending agents, e.g. sodium carboxymethyl cellulose, methyl cellulose, hydroxypropyl cellulose, sodium alginate, polyvinylpyrrolidone, gum tragacanth or acacia gum; dispersing and wetting agents, e.g. polyoxyethylene stearate, heptadecaethyleneoxycetanol, polyoxyethylene sorbitol mono-oleate, polyoxyethylene sorbitan mono-oleate or lecithin; preservatives, e.g. methyl or propylhydroxybenzoates; flavoring agents; sweeteners, e.g. sucrose, lactose, sodium cyclamate, dextrose and invert sugar syrup.

Oily suspensions contain, e.g., arachis, olive, sesame, coconut or paraffin oil, and thickeners, such as beeswax, hard paraffin or cetyl alcohol; further, sweeteners, flavorings and anti-oxidants.

Water-dispersible powders and granulates contain the medicaments in admixture with e.g., dispersing, wetting and suspending agents, such as those previously mentioned, and with sweetener, flavoring and coloring matter.

Emulsions contain, e.g., olive, arachis or paraffin oil besides emulsifying agents, such as acacia gum, gum tragacanth, phosphatides, sorbitan mono-oleate, polyoxyethylene sorbitan mono-oleate, sweetener and flavoring.

For the parenteral administration of the medicaments, sterile-injectable aqueous suspensions, isotonic salt solutions or other sterile solutions which contain dispersing or wetting agent and/or pharmacologically-compatible diluent, e.g. propylene glycol or butylene glycol, are suitable.

The active substance(s) are, where appropriate, also formulated with one or more of the stated excipients or additives in micro-encapsulated form.

When the substitued pyridazines according to the invention and/or their acid-addition salts are intended to be used for treating hypertension, the pharmaceutical preparations also optionally contain one or more other pharmacologically-active constituents of other medicament groups, such as other anti-hypertensive agents, $\beta$-receptor blockers, diuretics, salidiuretics, alkaloids, etc., such as dihydralazine, propranolol, labetalol, Mefruside, Clopamide, spironolactone, chlorothalidone, forosemide, polythiazide, hydrochlorothiazide, reserpine, dihydroergocristine, rescinnamine, rauwolfia whole alkaloids, etc.

A further aspect of the invention is a process for the preparation of substituted pyridazines of formula I, which process is characterized by reacting a pyridazine of formula II with a hydrazine derivative of formula III $$H_2N—R^1 \qquad \text{(III)},$$

wherein $R^1$ has its previously-stated meaning, and, where appropriate, is subsequently converted into the acid-addition salts, or the obtained reaction products of formula I (in which products $R^1$ represents —$NHR^3$ and $R^3$ represents a hydrogen atom) are subsequently derivatized or substituted and/or converted into their acid-addition salts; or that a pyridazine of formula II' is reacted with a compound of formula VII, $$R^2—C(=X)Y \qquad \text{(VII)}$$

wherein $R^2$ and X have their previously-stated meanings and Y represents a leaving group, or (when $R^2$ is —$NHR^7$ and $R^7$ denotes an alkyl or aryl group) with a heterocumulene VIII, $$R^7—N=C=X \qquad \text{(VIII)},$$

wherein $R^7$ represents an alkyl or aryl group and X denotes an oxygen or a sulfur atom, and, where appropriate, is converted into an acid-addition salt, or the obtained reaction product of formula I, wherein $R^1$ represents —$NHR^3$ and $R^3$ represents a hydrogen atom, is subsequently derivatized or substituted and/or converted into an acid-addition salt.

In order to prepare compounds of the more-restricted groups of embodiments, corresponding starting materials are reacted.

The reaction of a pyridazine II with a hydrazine derivative III is carried out according to processes known per se. The transient or leaving group Z is, for example, an alkoxy group, such as methoxy or ethoxy, or mercapto or alkyl mercapto, such as methylmercapto, or an alkylsulfinyl or alkylsulphonyl, such as methylsulfinyl or ethylsulphonyl, or a halogen atom, such as a chlorine atom. When Z is a halogen atom, preferably a bromine or chlorine atom, the reaction is expediently effected in the presence of an acid-binding agent (proton acceptor). Suitable as such are, for example, alkali metal hydroxides, such as sodium hydroxide and potassium hydroxide; or alkali metal carbonates, such as sodium carbonate and potassium carbonate; or tertiary amines, such as pyridine, triethylamine and N-ethyldiisopropylamine. Where appropriate, compound III is optionally used as a proton acceptor. The reaction is, in such case, carried out with, for example, a five-fold to ten-fold excess of III, with reference to compound II.

The reaction is carried out in suitable, expediently inert, preferably polar, solvent, such as a lower alkanol, e.g. methanol, ethanol or isopropanol, or open-chain or cyclic ethers, e.g. diethyleneglycoldimethyl ether, dioxan or tetrahydrofuran. Where appropriate, an excess of compound III optionally serves as solvent.

The reaction temperature may be varied within wide limits, e.g. from 20° to 150° C.; temperatures between 80° and 120° C. are preferred. The reaction time is between 1 and 20 hours under normal pressure.

The reaction of II with III is preferred over that of II' with VII or VIII.

The reaction of a pyridazine II' with a compound of formula VII is carried out according to processes known per se. The leaving group Y is, for example, an alkoxy group or a halogen atom, preferably a chlorine atom. The reaction is expediently effected in an inert, anhydrous solvent, e.g. a chlorinated hydrocarbon, such as chloroform or 1,2-dichloroethane. When Y is a halogen atom, the reaction is expediently effected in the presence of an acid-binding agent (proton acceptor), e.g. an alkali-metal carbonate, such as sodium or potassium carbonate, or a tertiary amine, such as triethylamine. The reaction temperature is, e.g., between −10° and 30° C., in particular between 0° and 20° C. The protection of the hydrazine group may be effected by conversion into the hydrazone, from which the hydrazine can be liberated by acid hydrolysis under mild conditions. The reaction of a pyridazine II' with a heterocumulene VIII is expediently effected in inert, anhydrous solvent, e.g. chlorinated hydrocarbon, such as dichloromethane, or open-chain or cyclic ether, such as diethyl ether or tetrahydrofuran, or aromatic hydrocarbon, such as benzene or toluene. The reaction temperature is, e.g., between −10° and 30° C., in particular between 0° and 20° C.

The substitution or the derivatization or the conversion into an acid-addition salt is carried out according to processes known to one skilled in the art.

Substitution is effected, for example, by acylation. This is carried out, e.g., through reaction with an appropriate acid anhydride or acid halide in inert solvent, such as chlorinated hydrocarbon, such as chloroform or methylene chloride; acetonitrile; cyclic or open-chain ether, such as dioxan, tetrahydrofuran or diethyl ether (cf., e.g., Houben Weyl, Vol. 8, p. 655 ff.).

The derivatization of a pyridazine of formula I, wherein $R^1$ represents —$NH_2$, to obtain a pyridazine of formula I, wherein $R^1$ is —$N=C(R^8)R^9$ and A, $R^2$ and X have their previously-ascribed meanings, is effected through reaction with an oxo compound of formula IV

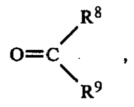

(IV)

wherein $R^8$ and $R^9$ have their previously-noted meanings, with addition, where appropriate, of a polar organic solvent (which is inert under the reaction conditions), for example a lower alkanol, such as methanol, ethanol or isopropanol, or an open-chain or cyclic ether, such as diethyleneglycoldimethyl ether, tetrahydrofuran or dioxan. The reaction mixture is kept for from 5 minutes to 20 hours, with appropriate heating, at a temperature of from about 0° C. to boiling temperature and subsequently evaporated to dryness, or the crude product is crystallized out directly or after substantial concentration of the solution. This synthesis route is preferred over the previously-described one-step variant which starts with a pyridazine II and a hydrazine derivative III, wherein $R^1$ is $-N{=}C(R^8)R^9$.

Acid-addition salts are obtained by dissolving a free base in a suitable solvent, e.g. a chlorinated hydrocarbon, such as methylene chloride or chloroform, or a low-molecular-weight aliphatic alcohol (ethanol, isopropanol), which contains the desired acid, or to which the desired acid is subsequently added. The salts are obtained through filtration, reprecipitation, precipitation with a non-solvent for the addition salt or through solvent evaporation.

Starting compounds II according to the invention, which represent new and interesting intermediate products for the synthesis of compounds I, are prepared according to various processes known per se. Thus, they are obtained through the reaction of a pyridazinone of formula V

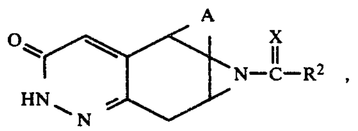

(V)

wherein

X stands for an oxygen atom, $R^2$ represents an alkoxy group and

A has its previously-ascribed meaning, with a suitable halogenating agent, such as phosphorus oxychloride, phosphorus tri- or penta-chloride, phosphorus oxybromide, oxalyl chloride or triphenylphosphine/carbon tetrachloride, where appropriate through subsequent exchange of the halogen atom for another leaving group Z (for example for an alkoxy group, such as methoxy, through reaction with a sodium alkanolate, such as sodium methanolate; or for an alkylmercapto group, such as methylmercapto, through reaction with a sodium alkanethiolate, such as sodium methanethiolate; or for an alkylsulfinyl or alkylsulfonyl group, through introduction of an alkylmercapto group, such as a methylmercapto group and its subsequent oxidation, for example with an equivalent amount of hydrogen peroxide). The reaction is effected, for example, in inert solvent, e.g. hydrocarbon, such as benzene or toluene, at a temperature of up to 150° C. [analogously to H. E. Baumgarten, P. L. Creger and C. H. Villars, *J. Amer. Chem. Soc.*, 80, 6609 (1958)].

Starting compounds of formula II are further obtained through reaction of a pyridazine of formula VI, (wherein Z and A have their previously-ascribed meanings), with a compound of type VII $$R^2{-}C({=}X)Y \qquad (VIII),$$

wherein $R^2$ and X have their previously-ascribed meanings and

Y represents a transient group, preferably a halogen atom.

The reaction is expediently carried out in an inert solvent, e.g. a chlorinated hydrocarbon, such as chloroform or ethylene chloride, in the presence of an acid-binding agent, e.g. an alkali metal carbonate, such as sodium or potassium carbonate, or a tertiary amine, e.g. triethylamine or pyridine.

When $R^2$ is $-N(R^6)R^7$, with $R^6$ denoting a hydrogen atom (—H) and $R^7$ denoting an alkyl, phenalkyl or aryl radical, an initial product II is further obtained through reaction of a heterocumulene VIII $$R^7{-}N{=}C{=}X \qquad (VIII),$$

(wherein $R^7$ and X have their previously-ascribed meanings), with a pyridazine VI.

The reaction is expediently carried out in an inert solvent, e.g. a hydrocarbon, such as benzene and cyclohexane, or in an ether, such as diethyl ether, or in a chlorinated hydrocarbon, such as methylene chloride.

Starting compounds II' according to the invention, which represent new and interesting intermediate products for the synthesis of compounds I, are obtained by reacting pyridazines of formula VI with hydrazine derivatives III, $$H_2N{-}R^1 \qquad (III)$$

wherein $R^1$ has its previously-ascribed meaning, and, where appropriate, converting the reaction product into an acid-addition salt. The obtained reaction product of formula II' (wherein $R^1$ represents $-NHR^3$ and $R^3$ represents a hydrogen atom) are optionally subsequently derivatized or substituted and/or converted into acid-addition salts. The reaction is carried out as previously described (reaction of compounds II with compounds III).

Compounds of formula V, in which X is an oxygen atom, $R^2$ represents an alkoxy group and A has its previously-ascribed meaning, are prepared from a dihydropyridazinone of formula IX

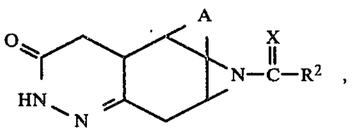

(IX)

(wherein X is an oxygen atom, $R^2$ represents an alkoxy group and A has its previously-ascribed meaning), according to conventional dehydrogenation processes.

Chloranil, 2,3-dichloro-5,6-dicyano-p-benzoquinone, N-bromosuccinimide and, preferably, bromine are suitable dehydrogenating agents. Halogenated hydrocarbons, for example chloroform or ethylene chloride, are chiefly used as solvent. The preferred reaction temperature is the boiling point of the respective solvent [analogously to H. E. Baumgarten, P. L. Creger and C. H. Villars, *J. Amer. Chem. Soc.*, 80, 6609 (1958)].

Pyridazines VI according to the invention are obtained, for example, by halogenating pyridazinones X

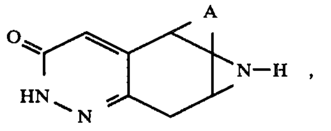

(X)

(wherein A has its previously-ascribed meaning) and, optionally, subsequently converting the obtained reaction product into an acid-addition salt. Suitable halogenating agents are, for example, phosphorus oxytrichloride or bromide. The reaction is expediently effected in an inert solvent, e.g. hydrocarbon, such as benzene and toluene, or without solvent with an excess of the halogenating agent. The reaction temperature is up to 120° C.

Compounds of formula IX are prepared from aza-bicycloalkanones of formula XI

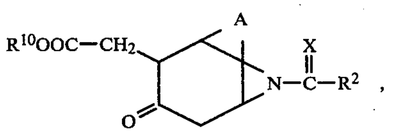

(XI)

wherein
X is an oxygen atom,
$R^2$ represents an alkoxy group,
A has its previously-ascribed meaning and
$R^{10}$ symbolizes an alkyl radical,
through reaction with hydrazine hydrate/glacial acetic acid or a hydrazine salt according to processes known to the man skilled in the art. The reaction is effected preferably in a polar inert solvent, for example ethanol. The temperature is, e.g., in the range between 70° and 110° C., in particular at the boiling temperature of the reaction mixture.

Compounds of formula X are prepared, for example, from pyridazinones V, wherein X is an oxygen atom, $R^2$ represents an alkoxy group and A has its previously-ascribed meaning. The splitting off of the

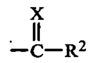

group is effected according to processes known to one skilled in the art, through heating of V in acid medium, e.g. in hydrochloric acid, or in alkaline manner, e.g. through heating with an alkali metal hydroxide, such as sodium or potassium hydroxide, in a higher-boiling alcohol, such as n-butanol.

Compounds of formula XI are prepared, according to processes known to one skilled in the art, by hydrolysis from enamines XII

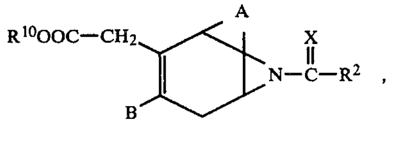

(XII)

wherein
X is an oxygen atom,
$R^2$ represents an alkoxy group,
A and $R^{10}$ have previously-stated meanings and
B represents a secondary, preferably cyclic, amino group, e.g. a pyrrolidino, morpholino or piperidino group.

The hydrolysis is effected through heating with water and, where appropriate, with addition of a dilute solution of alkali, such as sodium hydroxide solution or ammonia solution, or with addition of a dilute acid, such as hydrochloric acid.

Compound IX is also prepared by a process known to one skilled in the art by reacting an enamine XII with hydrazine hydrate/glacial acetic acid or with a hydrazine salt in a polar, aprotic solvent, for example acetonitrile, at a temperature between 70° and 110° C., preferably at the boiling temperature of the reaction mixture.

Compound XII is obtained according to processes known to one skilled in the art by reacting an enamine XIII

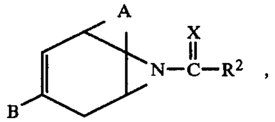

(XIII)

wherein
X is an oxygen atom,
$R^2$ represents an alkoxy group and
A and B have their previously-ascribed meanings,
with a halogen acetic acid alkyl ester in an absolute, preferably polar, solvent, such as acetonitrile or ethanol, in the presence of a proton acceptor, e.g. potassium carbonate or a non-alkylatable tertiary organic amine, such as diisopropylethylamine or dicyclohexylethylamine [cf. G. Stork, R. Terrell and J. Szmuszkovicz, *J. Amer. Chem. Soc.*, 76, 2029 (1954)].

Compounds XIII are obtained according to processes known to one skilled in the art by reacting an aza-bicycloalkanone of formula XIV

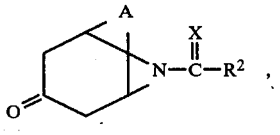

(XIV)

wherein
X is an oxygen atom,
$R^2$ represents an alkoxy group and
A has its previously-stated meaning,
with an appropriate secondary amine, such as pyrrolidine, morpholine or piperidine, in the presence of a strongly dehydrating Lewis acid, preferably titanium tetrachloride, in an inert hydrocarbon, such as hexane or petroleum ether, at from 0° to 50° C. [cf. W. H. White and H. Weingarten, *J. Org. Chem.*, 32, 213 (1967)].

Compounds of formula XIV are prepared according to processes known to one skilled in the art through reaction of an aza-bicycloalkanone of formula XV

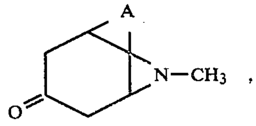

(XV)

(wherein A has its previously-stated meaning) with a compound of the formula

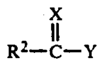

wherein
X is an oxygen atom,
$R^2$ represents an alkoxy group and
Y represents a leaving group, e.g. a halogen atom.

The reaction is preferably effected through heating in an inert solvent, e.g. a hydrocarbon, such as benzene or toluene, or in a halogen hydrocarbon, such as chloroform, 1,2-dichloroethane or trichloroethane, and (where appropriate) under an inert gas atmosphere, to a temperature between 80° to 120° C., preferably to the boiling temperature of the reaction mixture. The reaction duration may be from 10 to 36 hours [cf. Th. A. Montzka, J. D. Matiskella and R. A. Partyka, *Tetrahedron Letters,* 1974, 1325-1327].

The compounds of formula XV are prepared according to A. C. Cope, H. L. Dryden, Jr., and Ch. F. Howell [Org. Synth., Coll. Vol. IV, 816] or C. Schöpf and G. Lehmann [Ann. 518, 1 (1935)].

The following examples illustrate the invention more fully, without restricting it. The abbreviations m.p. and b.p. denote melting point and boiling point, respectively.

EXAMPLE 1

3-hydrazino-5,7-propano-5,6,7,8-tetrahydro-6-pyrido[4,3-c]pyridazine carboxylic acid ethyl ester $R^1 = -NH_2$, $R^2 = -OC_2H_5$, $A = -(CH_2)_3-$, $X = O$ A suspension of 17.5 g of 3-chloro-5,7-propano-5,6,7,8-tetrahydro-6-pyrido[4,3-c]pyridazine carboxylic acid ethyl ester (a) in 150 ml of hydrazine hydrate is heated to boiling under reflux for 1 hour at an oil-bath temperature of 110° C., under a nitrogen atmosphere and with stirring; after about 10 minutes, complete solution occurs; the thus-obtained yellow solution is concentrated in a vacuum, and the residue is taken up on chloroform. The resulting solution is washed twice with water, dried over sodium sulfate, filtered and evaporated to dryness in a vacuum. The light-yellow, solidified foam which remains behind is taken up in 80 ml of methanol. After addition of 7.21 g of fumaric acid and brief stirring, a clear light-yellow solution is obtained. From this solution the title compound crystallizes out as fumarate within 12 hours at 0° C. After suction filtration, washing with a little ice-cold methanol and acetonitrile and drying at 40° C., 19 g (79 percent) of the fumarate [melting point: 148° to 150° C. (decomp.)] are obtained.

The starting compound is prepared, e.g., as follows:

(a) 3-chloro-5,7-propano-5,6,7,8-tetrahydro-6-pyrido [4,3-c]pyridazine carboxylic acid ethyl ester 22.75 g of 5,7-propano-2,3,5,6,7,8-hexahydro-3-oxo-6-pyrido [4,3-c]pyridazine carboxylic acid ethyl ester (b) are suspended in 100 ml of phosphorus oxytrichloride and heated to a boil under reflux for 1 hour. After cooling, excess phosphorus oxytrichloride is distilled off in a vacuum. Obtained brown residue is poured onto 150 g of ice and stirred. The resulting acid aqueous solution is filtered and then extracted three times with methylene chloride. The united organic phases are washed with water (through addition of saturated sodium hydrogen carbonate solution in the aqueous phase a pH value of 8 is set up), dried over sodium sulfate and then concentrated to dryness in a vacuum. The residue is taken up in a 9:1 mixture of methylene chloride/methanol, filtered over silica gel and eluted with methylene chloride/methanol (9:1) until no product is any longer detected by thin-layer chromatography in the filtrate which runs off. The filtrate is concentrated in a vacuum, and the residue is recrystallized from 25 ml of carbon tetrachloride and 5 ml of n-hexane to yield 18.5 g (76.5 percent) of (a)—m.p. 113° to 113.5° C.

(b) 5,7-propano-2,3,5,6,7,8-hexahydro-3-oxo-6-pyrido[4,3-c]pyridazine carboxylic acid ethyl ester 113 g of 5,7-propano-2,3,4,4a,5,6,7,8-octahydro-3-oxo-6-pyrido[4,3-c]pyridazine carboxylic acid ethyl ester (c) are dissolved in 490 ml of chloroform and heated to a boil under reflux. 68.1 g of bromine (dissolved in 130 ml of chloroform) are added dropwise, with stirring, within 1.5 hours into the boiling solution. After a further 2.5 hours' stirring under reflux, cooling is effected and 190 ml of water are added. With stirring, the aqueous phase is adjusted to pH 7 with saturated sodium hydrogen carbonate solution, and then the chloroform phase is separated off. The aqueous phase is extracted a further two times with chloroform; the united chloroform phases are dried over magnesium sulfate. After the drying agent has been filtered off, the chloroform is drawn off in a vacuum and the residue (116.7 g) is processed without further purification.

(c) 5,7-propano-2,3,4,4a,5,6,7,8-octahydro-3-oxo-6-pyrido[4,3-c]pyridazine carboxylic acid ethyl ester 260 g of 3-(1-pyrrolidinyl)-9-axabicyclo[3,3,1]-non-2-ene-9-carboxylic acid ethyl ester (d) and 127.1 g of N,N-diisopropylethylamine are dissolved in 750 ml of absolute acetonitrile. To this solution a solution of 164.2 g of bromoacetic acid ethyl ester in 770 ml of absolute acetonitrile is added dropwise, under a nitrogen atmosphere and with stirring, at from 25° to 30° C. within 2.5 hours. The mixture is slowly heated within one hour and then heated to a boil under reflux for 4.5 hours. After cooling, 54.2 g of hydrazine hydrate and then 65 g of glacial acetic acid are added. After a further 2.5 hours under reflux and subsequent cooling, the solvent is evaporated off in a vacuum. After dissolving the residue in chloroform, washing is effected twice with water, once with saturated sodium hydrogen carbonate solution and twice again with water, followed by drying over sodium sulfate. After the drying agent has been filtered off, the solution is evaporated to dryness. The residue is dissolved in 250 ml of hot carbon tetrachloride (70° C.), and 175 ml of n-hexane are slowly added in the heat (60° C.). After several days' standing at 0° C., the product which has crystallized out is suction filtered and washed with a little cold carbon tetrachloride. After drying (65° C., in a vacuum), 113 g (43.3 percent) of (c) [m.p. 123° to 124° C.] are obtained.

(d) 3-(1-pyrrolidinyl)-9-azabicyclo[3,3,1]non-2-ene-9-carboxylic acid ethyl ester At room temperature, under a nitrogen atmosphere and with stirring, a solution of 110 g of titanium tetrachloride in 450 ml of petroleum ether is added dropwise, within 2.5 hours, to a solution of 223 g of 9-azabicyclo-[3,3,1]nonan-3-one-9-carboxylic acid ethyl ester (e) and 300 g of pyrrolidine in 2.5 liters of absolute petroleum ether (b.p. 50° to 70° C.). The mixture is stirred for 24 hours. The light-yellow precipitate formed is filtered, suspended in benzene, suction filtered and washed with benzene. The united filtrates are concentrated in a vacuum; the orange-red oil which remains behind is purified through vacuum distillation to obtain 260 g (93.5 percent) of yellow, viscous oil (b.p. 140° C. at 6.7 Pa.)

(e) 9-azabicyclo-[3,3,1]nonan-3-one-9-carboxylic acid ethyl ester 186.8 g of pseudo-pelletierine and 264 g of freshly distilled chloroformic acid ethyl ester are slowly heated to a boil in 1 liter of absolute toluene within one hour. A vigorous evolution of gas sets in. The mixture is heated to a boil under reflux for a further 16 hours, then cooled and filtered. The filtrate is concentrated in a vacuum, and the residue is purified through vacuum distillation to obtain 223 g (86.5 percent) of light-yellow oil (b.p. 101° C. at 2.7 Pa.)

EXAMPLE 2

3-isopropylidenehydrazino-5,7-propano-5,6,7,8-tetrahydro-6-pyrido-[4,3-c]pyridazine carboxylic acid ethyl ester A suspension of 5.8 g of 3-chloro-5,7-propano-5,6,7,8-tetrahydro-6-pyrido[4,3-c]pyridazine carboxylic acid ethyl ester (cf. Example 1*a*) in 50 ml of hydrazine hydrate is stirred under a nitrogen atmosphere for 1 hour at an oil-bath temperature of 110° C. The yellow solution so obtained is completely concentrated in a vacuum, and the residue is taken up in chloroform. The chloroform solution is washed twice with water, dried over sodium sulfate, filtered, and evaporated to dryness in a vacuum. The light-yellow, solidified foam which remains behind is dissolved in 15 ml of acetone, and the resultant solution is heated to the boil under reflux for 30 minutes. The bulk of the solvent is evaporated off in a vacuum, and diethyl ether is added to the residue. After a short time, the title compound crystallizes out. After suction filtration and washing with diethyl ether, 4.6 g (70 percent) of the title compound (m.p. 148° to 150° C.) are obtained.

EXAMPLE 3

3-[1-(p-chloro)phenylethylidenehydrazino]-5,7-propano-5,6,7,8-tetrahydro-6-pyrido[4,3-c]pyridazine carboxylic acid ethyl ester 1.2 g of the fumarate of 3-hydrazino-5,7-propano-5,6,7,8-tetrahydro-6-pyrido[4,3-c]pyridazine carboxylic acid ethyl ester (Example 1) and 0.52 g of 4-chloroacetophenone are dissolved in 10 ml of absolute ethanol and heated to a boil under reflux for 4 hours. After the solvent has been evaporated off in a vacuum, the residue is recrystallized from methanol. 1.4 g (97.5 percent) of the title compound are obtained as semifumarate (m.p. 201° to 202° C.).

EXAMPLE 4

3-isopropylidenehydrazino-5,7-ethano-5,6,7,8-tetrahydro-6-pyrido[4,3-c]-pyridazine carboxylic acid ethyl ester A suspension of 4.8 g of 3 -chloro-5,7-ethano-5,6,7,8-tetrahydro-6-pyrido[4,3-c]pyridazine carboxylic acid ethyl ester (a) in 40 ml of hydrazine hydrate is stirred at 110° C. for one hour under a nitrogen atmosphere. The yellow solution formed is evaporated to dryness in a vacuum. The residue is taken up in chloroform, the chloroform solution is washed twice with water, dried over sodium sulfate and filtered. After concentration of the filtrate in a vacuum, the residue is dissolved in 20 ml of acetone and heated to a boil under reflux for one hour. The solution is largely concentrated, and diethyl ether is added to the residue. After a short time, the title compound crystallizes out. 3.9 g (72 percent) of the title compound (m.p. 153° to 156° C.) are thus obtained. The starting compound is prepared as follows:

(a)

3-chloro-5,7-ethano-5,6,7,8-tetrahydro-6-pyrido[4,3-c]pyridazine carboxylic acid ethyl ester 12 g of 5,7-ethano-2,3,5,6,7,8-hexahydro-3-oxo-6-pyrido[4,3-c]pyridazine carboxylic acid ethyl ester (b) are dissolved in 100 ml of phosphorus oxytrichloride and heated to a boil under reflux for one hour. After cooling, the excess phosphorus oxytrichloride is distilled off in a vacuum. The brown residue is taken up in chloroform and stirred with ice water; the aqueous phase is then neutralized with ammonia solution and subsequently extracted twice with chloroform. The united chloroform phases are washed twice with water, dried over magnesium sulfate and filtered. After concentration of the filtrate in a vacuum, the residue is recrystallized from carbon tetrachloride/petroleum ether to obtain 8.94 g (69.5 percent) of (a) [m.p. 84° C. (decomp.)].

(b)

5,7-ethano-2,3,5,6,7,8-hexahydro-3-oxo-6-pyrido[4,3-c]pyridazine carboxylic acid ethyl ester A solution of 2.02 g of bromine in 10 ml of chloroform is slowly added dropwise to a boiling solution of 3.18 g of 5,7-ethano-2,3,4,4a,5,6,7,8-octahydro-3-oxo-6-pyrido[4,3-c]pyridazine carboxylic acid ethyl ester (c) in 20 ml of chloroform. The mixture is heated to a boil under reflux for one hour. After cooling, ice water is added. The aqueous phase is neutralized with sodium hydrogen carbonate and extracted with chloroform. The united chloroform phases are dried over magnesium sulfate and filtered. The oil remaining after evaporation of the solvent in a vacuum is recrystallized from carbon tetrachloride/petroleum ether to obtain a yield of 2.3 g (73.2 percent) of (b)—m.p. 175° to 177° C.

(c)

5,7-ethano-2,3,4,4a,5,6,7,8-octahydro-3-oxo-6-pyrido[4,3-c]-pyridazine carboxylic acid ethyl ester 35.6 g of 3-(1-pyrrolidinyl)-8-azabicyclo[3,2,1]-oct-3-ene-8-carboxylic acid ethyl ester (d) and 18.4 g of N,N-diisopropylethylamine are dissolved, under a nitrogen atmosphere, in 100 ml of anhydrous acetonitrile. A solution of 23.7 g of bromoacetic acid ethyl ester in 100 ml of anhydrous acetonitrile is added dropwise within 45 minutes, with vigorous stirring. Subsequently, after slow warming, heating to a boil under reflux is effected for 1 hour. The mixture is cooled and 7.8 g of hydrazine hydrate and 9.4 g of acetic acid are slowly added successively; the mixture is again heated to a boil and kept at boiling temperature for 1 hour. After the solvent is distilled off in a vacuum, the residue remaining behind is dissolved in 200 ml of chloroform, washed twice with (in each case) 100 ml of water, with sodium hydrogen carbonate solution and again with water, dried over sodium sulfate and filtered. The filtrate is concentrated in a vacuum and the residue is chromatographed over silica gel (chloroform/methanol 99:1). The thin-layer chromatographically uniform fractions are evaporated in a vacuum, and the residue is recrystallized from carbon tetrachloride/petroleum ether to obtain 11.4 g (35 percent) of (c)—m.p. 128° to 131° C.

(d)
3-(1-pyrrolidinyl)-8-azabicyclo[3,2,1]oct-3-ene-8-carboxylic acid ethyl ester 36.6 g of 8-azabicyclo[3,2,1]octan-3-one-8-carboxylic acid ethyl ester (e) are dissolved in 500 ml of absolute petroleum ether, and 52.8 g of pyrrolidine are added. A solution of 19.4 g of titanium tetrachloride in 100 ml of petroleum ether is added dropwise within 70 minutes, with vigorous stirring. With slight warming of the solution, a light-yellow precipitate is immediately precipitated. After 110 hours' stirring at room temperature, the precipitate is allowed to settle and the yellow petroleum ether solution is decanted. The precipitate is suspended in 250 ml of anhydrous benzene, suction filtered, and washed with benzene. The united organic phases are concentrated in a vacuum; the oil which remains behind is purified by vacuum distillation to obtain 42.8 g (92.2 percent) of (d) as a light-yellow, viscous oil (b.p. 125° to 128° C. at 8 Pa.).

(e) 8-azabicyclo[3,2,1]octan-3-one-8-carboxylic acid ethyl ester 56.5 g of tropinone are dissolved in 330 ml of anhydrous benzene and heated to 70° C. under a nitrogen atmosphere. A solution of 88 g of freshly-distilled ethyl chloroformate in 200 ml of benzene is added dropwise within one hour, with stirring. After a further 4 hours' heating under reflux, cooling is effected, followed by filtration; the filtrate is concentrated in a vacuum, and the residue is purified by vacuum distillation to obtain 70.75 g (88.4 percent) of (e) as colorless oil (b.p. 91° to 93° C. at 12 Pa.)

EXAMPLE 5

6-benzoyl-3-hydrazino-5,7-propano-5,6,7,8-tetrahydropyrido[4,3-c]-pyridazine 8.6 g of 6-benzoyl-3-chloro-5,7-propano-5,6,7,8-tetrahydropyrido[4,3-c]pyridazine (a) are suspended under a nitrogen atmosphere in a mixture consisting of 28 ml of dioxan and 28 ml of hydrazine hydrate and heated to a boil. The mixture is kept at boiling temperature for 9 hours, cooled and concentrated to dryness in a vacuum. The residue is distributed between dichloromethane and water; the organic phase is washed three times with water, dried over magnesium sulfate and filtered. The filtrate is concentrated in a vacuum and dried to constant weight; 8.6 g of crude base are obtained as solidified foam. The crude base is dissolved in 8 ml of methanol, and a suspension of 3.1 g of fumaric acid in 36 ml of methanol are added, with stirring. Within a short time a clear solution is formed; from this solution, after addition of ethyl acetate, rubbing and cooling, the title compound crystallizes out as fumarate [m.p. 157° C. (decomposition)].

The starting compound is prepared as follows:

(a)
6-benzoyl-3-chloro-5,7-propano-5,6,7,8-tetrahydropyrido[4,3-c]-pyridazine 5.3 g of triethyl amine and 5 g of benzoyl chloride dissolved in 30 ml of 1,2-dichloroethane are successively added dropwise, with ice cooling and stirring, to 7.3 g of 3-chloro-5,7-propano-5,6,7,8-tetrahydropyrido[4,3-c]pyridazine (b) in 58 ml of 1,2-dichloroethane. After 2 hours' stirring at room temperature, 70 ml of water are added, the aqueous phase is washed once with (in each case) 1 N hydrochloric acid solution, sodium hydrogen carbonate solution and water, dried over magnesium sulfate and filtered. The filtrate is concentrated in a vacuum, the residue is taken up in 25 ml of ethanol and rubbed. The product (which has crystallized out after cooling) is suction filtered, washed with ethanol and dried at 80° C. in a vacuum to obtain 8.62 g (78.9 percent) of (a)—m.p. 197° to 198.5° C.

(b)
3-chloro-5,7-propano-5,6,7,8-tetrahydropyrido[4,3-c]pyridazine 11.08 g of 3-oxo-5,7-propano-2,3,5,6,7,8-hexahydropyrido[4,3-c]pyridazine hydrochloride (c) and 60.5 ml of phosphorus oxide trichloride are heated to a boil under reflux for 7 hours. The excess phosphorus oxide trichloride is distilled off in a vacuum, and ice water is added to the oil which remains behind. The aqueous solution is adjusted to pH 11 with concentrated ammonia solution and extracted four times with chloroform. The united chloroform solutions are dried over magnesium sulfate, filtered, stirred with activated charcoal at room temperature and filtered again. The product, which crystallizes after concentration of the filtrate, is dried in a vacuum and further reacted without further purification. Yield: 9.46 g (92.8 percent); m.p.: 146° to 148° C.

(c)
3-oxo-5,7-propano-2,3,5,6,7,8-hexahydropyrido[4,3-c]pyridazine hydrochloride 14.5 g of 3-oxo-5,7-propano-2,3,5,6,7,8-hexahydro-6-pyrido[4,3-c]pyridazine carboxylic acid ethyl ester (cf. Example 1b) are dissolved in 77 ml of concentrated hydrochloric acid and heated to the boil under reflux for 30 hours. The cooled solution is extracted once with chloroform, and the aqueous phase is evaporated to dryness in a vacuum. 50 ml of methanol are added to the residue. Rubbing is effected. The suspension is heated to a boil, cooled and suction filtered. After drying in a vacuum, 11.2 g (89 percent) of (c) [m.p. 360° to 362° C. (decomp.)] are obtained.

EXAMPLE 6

6-benzoyl-3-isopropylidenehydrazino-5,7-propano-5,6,7,8-tetrahydropyrido[4,3-c]pyridazine A mixture consisting of 4.85 g of 6-benzoyl-3-chloro-5,7-propano-5,6,7,8-tetrahydropyrido[4,3-c]pyridazine (cf. Example 5a), 16 ml of hydrazine hydrate and 16 ml of dioxan is heated to a boil under reflux for 14 hours. The solvent and the excess hydrazine hydrate are distilled off in a vacuum. The residue is dried in a high vacuum and dissolved in 50 ml of dichloromethane. The resulting solution is washed twice with water, dried over magnesium sulfate and filtered. The residue remaining behind after concentration of the filtrate in a vacuum is dissolved in 12 ml of acetone and heated to a boil under reflux for 20 minutes. The solvent is distilled off in a vaccum, and the residue is recrystallized from acetone diethyl ether to obtain 5.35 g (81.5 percent) of title compound [m.p. 211° to 212° C. (from acetonitrile)].

EXAMPLE 7

6-benzoyl-3-(2-butylidenehydrazino)-5,7-propano-5,6,7,8-tetrahydropyrido[4,3-c]pyridazine Analogously to Example 6, from 4.95 g of 6-benzoyl-3-chloro-5,7-propano-5,6,7,8-tetrahydropyrido[4,3-c]pyridazine, 16 ml of hydrazine hydrate, 16 ml of dioxan and 14 ml of 2-butanone, 3.5 g (62 percent) of the title compound [m.p. 180° to 182° C. (from acetonitrile)] are obtained.

EXAMPLE 8

3-isopropylidenehydrazine-6-pivaloyl-5,7-propano-5,6,7,8-tetrahydropyrido[4,3-c]pyridazine A mixture consisting of 3.84 g of 3-chloro-6-pivaloyl-5,7-propano-5,6,7,8-tetrahydropyrido[4,3-c]pyridazine (a), 13 ml of hydrazine hydrate and 13 ml of dioxan is heated to the boil under reflux for 12.5 hours. The solvent and excess hydrazine hydrate are distilled off in a vacuum. The residue is taken up with chloroform, the chloroform solution is washed twice with water, dried over magnesium sulfate and filtered. The filtrate is concentrated to dryness in a vacuum, the residue is dissolved in 30 ml of acetone and the solution is heated to the boil under reflux for 30 minutes. After concentration in a vacuum, the residue is recrystallized from acetonitrile/diisopropyl ether. 2.4 g (55.1 percent) of the title compound (m.p. 179° to 181.5° C.) are obtained.

The starting compound may be prepared as follows:

(a)

3-chloro-6-pivaloyl-5,7-propano-5,6,7,8-tetrahydropyrido[4,3-c]-pyridazine 2.17 g of triethyl amine and 1.9 g of pivaloyl chloride (dissolved in 25 ml of 1,2-dichloroethane) are successively added dropwise, with ice cooling and stirring, to 3 g of 3-chloro-5,7-propano-5,6,7,8-tetrahydropyrido[4,3-c]pyridazine (cf. Example 5b) in 25 ml of 1,2-dichloroethane. The solution is left to stand over night, washed twice with water, with 2 N hydrochloric acid solution, again with water and with sodium hydrogen carbonate solution, dried over sodium sulfate and concentrated to dryness in a vacuum. The residue (3.84 g, 91.4 percent) is further processed without purification.

EXAMPLE 9

3-isopropylidenehydrazino-5,7-propano-5,6,7,8-tetrahydro-6-pyrido-[4,3-c]pyridazine carboxylic acid N-methyl amide 4.25 g of 3-chloro-5,7-propano-5,6,7,8-tetrahydro-6-pyrido[4,3-c]pyridazine carboxylic acid N-methyl amide (a), 16 ml of hydrazine hydrate and 16 ml of dioxan are heated to a boil under reflux for 6 hours. Excess hydrazine hydrate and the solvent are distilled off in a vacuum; the residue is dried in a high vacuum and dissolved in hot acetone. During cooling, the title compound crystallizes out as the hydrochloride and is again recrystallized from acetone/methanol to obtain 3.68 g (68.4 percent) of the title compound [m.p. 200° to 201° C. (decomp.)].

The starting compound is prepared as follows:

(a)

3-chloro-5,7-propano-5,6,7,8-tetrahydro-6-pyrido[4,3-c]pyridazine carboxylic acid N-methyl amide A solution of 1.5 g of methyl isocyanate in 30 ml of 1,2-dichloroethane is added dropwise within 30 minutes, with stirring, to an ice-cooled solution of 5 g of 3-chloro-5,7-propano-5,6,7,8-tetrahydropyrido[4,3-c]-pyridazine (cf. Example 5b) in 60 ml of 1,2-dichloroethane. After a further 30 minutes' stirring at room temperature, the solvent is distilled off in a vacuum, and the foam (which remains behind) is dissolved in methanol. After rubbing and cooling, 5.3 g (83.3 percent) of (a) [m.p. 162° to 165° C.] are obtained.

EXAMPLE 10

3-(2-ethoxycarbonylhydrazino)-5,7-propano-5,6,7,8-tetrahydro-6-pyrido[4,3-c]pyridazine carboxylic acid ethyl ester 4.5 g of 3-chloro-5,7-propano-5,6,7,8-tetrahydro-6-pyrido[4,3-c]pyridazine carboxylic acid ethyl ester (cf. Example 1a) and 3.35 g of hydrazine carboxylic acid ethyl ester in 30 ml of dioxan are heated to the boil under reflux for 8.5 hours. Evaporation to dryness is effected in a vacuum. The residue is dissolved in chloroform. The chloroform solution is washed twice with water, dried over sodium sulfate and filtered. The filtrate is evaporated to dryness in a vacuum, and the foam which remains behind is dissolved in boiling ethanol. During cooling, the title compound crystallizes out. 2.17 g of the title compound (m.p. 180.5° to 182.5° C.) are thus obtained. From the mother liquor (after evaporation and crystallization from water/methanol) a further 1.95 g of the title compound (m.p. 180.5° to 183.5° C.) are obtained. Total yield: 4.12 g (78.8 percent).

EXAMPLE 11

3-hydrazino-5,7-propano-5,6,7,8-tetrahydro-6-pyrido[4,3-c]pyridazine carboxylic acid ethyl ester 0.513 g of embonic acid (1,1'-methylene-bis-2-hydroxy-3-naphthoic acid) in 2.54 ml of 1 N potassium hydroxide solution is added to a concentrated aqueous solution of 0.5 g of 3-hydrazino-5,7-propano-5,6,7,8-tetrahydro-6-pyrido[4,3-c]pyridazine carboxylic acid ethyl ester fumarate (cf. Example 1). The embonate of the title compound is instantly precipitated, is suction filtered after about 30 minutes, washed thorougly with water and dried at 40° C. in a vacuum to obtain 0.8 g (93 percent) of the embonate of the title compound [m.p. 179° C. (decomposition)].

EXAMPLE 12

3-Isopropylidenehydrazino-6-(N-phenylthiocarbamoyl)-5,7-propano-5,6,7,8-tetrahydropyrido[4,3-c]pyridazine 1.38 g of phenylisothiocyanate are added to a suspension of 2.5 g of 3-isopropylidenehydrazino-5,7-propano-5,6,7,8-tetrahydropyrido[4,3-c]pyridazine in 25 ml of dichloromethane, while stirring and ice-cooling. The yellowish solution which forms is stirred for a further 45 minutes and evaporated in vacuo.

The residue is recrystallized from ethanol/petroleum ether to give 3.5 g (90 percent) of the title compound of m.p. 133° C. (decomposition).

EXAMPLE 13

3-Isopropylidenehydrazino-6-(N-phenylcarbamoyl)-5,7-propano-5,6,7,8-tetrahydropyrido[4,3-c]pyridazine 2.73 g (92 percent) of the title compound of m.p. 232° C. (decomposition) are obtained from 2 g of 3-isopropylidenehydrazino-5,7-propano-5,6,7,8-tetrahydropyrido[4,3-c]pyridazine and 0.98 g of phenyl isocyanate by the procedure described in Example 12.

EXAMPLE 14

3-Isopropylidenehydrazino-5,7-propano-5,6,7,8-tetrahydropyrido[4,3-c]-pyridazine 20 g of 3-isopropylidenehydrazino-5,7-propano-5,6,7,8-tetrahydro-6-pyrido[4,3-c]pyridazine carboxylic acid ethyl ester are boiled under reflux in 120 ml of concentrated hydrochloric acid for 72 hours. After cooling, 200 ml of water and 6 N sodium hydroxide solution are added to pH 8–9. The aqueous solution is extracted twice with dichloromethane, and 6 N sodium hydroxide solution is added to pH 10–11. The solution is once more extracted with dichloromethane, and concentrated hydrochloric acid is added to pH 1. The residue remaining after concentration is taken up in acetone and dichloromethane. Solid potassium carbonate is added. The solution is filtered off and evaporated to dryness in vacuo. After recrystallizing the precipitate from ethanol, 5.81 g of the title compound of m.p. 219° to 222° C. are obtained.

EXAMPLE 15

3-isopropylidenehydrazino-5,7-propano-5,6,7,8-tetrahydro-6-pyrido-[4,3-c]pyridazine carboxylic acid ethyl ester 0.34 g of chloroformic acid ethyl ester is added dropwise, with ice-cooling and stirring, to a suspension of 1.0 g of 3-isopropylidenehydrazino-5,7-propano-5,6,7,8-tetrahydropyrido[4,3-c]-pyridazine and 0.35 g of triethylamine in 20 ml of anhydrous methylene chloride. The resulting orange-coloured solution is stirred for a further hour at room temperature, extracted twice with 10 ml of water and 3 ml of 0.1 N hydrochloric acid, dried over sodium sulphate and evaporated to dryness. The remaining foam is dissolved in hot acetone. After cooling of the solution, diethyl ether is added. 0.4 g of the title compound (m.p. 148°–150° C.) crystallizes out in the cold.

EXAMPLE 16

3-isopropylidenehydrazino-5,7-propano-5,6,7,8-tetrahydropyrido-[4,3-c]pyridazine A suspension of 2.1 g of 3-chloro-5,7-propano-5,6,7,8-tetrahydro-6-pyrido[4,3-c]-pyridazine in 25 ml of hydrazine hydrate is heated to the boil under reflux for 1.5 hours under a nitrogen atmosphere. After cooling and filtration, the filtrate is evaporated to dryness. The remaining residue is dissolved in 30 ml of acetone, heated to the boil for 30 minutes and evaporated to dryness again. The remaining oil is dissolved in 50 ml of methylene chloride/acetone (1:1) and washed with dilute potassium carbonate solution. The aqueous phase is extracted with methylene chloride. The combined organic phases are dried over potassium carbonate, filtered and evaporated to dryness. The residue is recrystallised from ethanol to obtain 1.63 g (66%) of the title compound, m.p. 219° to 221° C.

EXAMPLE 17

Tablets containing 10 mg of active compound 5.0 kg of 3-hydrazino-5,7-propano-5,6,7,8-tetrahydro-6-pyrido[4,3-c]pyridazine carboxylic acid ethyl ester fumarate, 50.0 kg of calcium sulphate dihydrate, 31.0 kg of maize starch and 3.0 kg of polyvinylpyrrolidone are moistened with 20 liters of water and the mixture is granulated through a sieve of 1.25 mm mesh width. The granules are dried down to a relative moisture content of 50–60% in a fluidized bed drier, and 8.0 kg of sodium carboxymethylcellulose, 2.0 kg of talc and 1.0 kg of magnesium stearate are added. The finished granules are pressed to form tablets weighing 200 mg and having a diameter of 8 mm.

EXAMPLE 18

Ampoules containing 22.5 mg of active compound 1.125 kg of 3-hydrazino-5,7-propano-5,6,7,8-tetrahydro-6-pyrido[4,3-c]pyridazine carboxylic acid ethyl ester fumarate are dissolved in 80 liters of doubly distilled water, and 4.337 kg of mannitol are added. The solution is made up to 100 kg with doubly distilled water, filtered through a filter under sterile conditions and filled into 2 ml ampoules.

EXAMPLE 19

10,000 capsules with an active compound content of 5 mg 50 g of 3-hydrazino-5,7-propano-5,6,7,8-tetrahydro-6-pyrido-[4,3-c]-pyridazine carboxylic acid ethyl ester fumarate, 945 g of microcrystalline cellulose and 5 g of amorphous silica (the active compound in a finely powdered form) are mixed thoroughly and filled into hard gelatine capsules of size 4.

EXAMPLE 20

250,000 retard capsules with an active compound content of 30 mg 1.1 kg of talc are suspended in a solution of 8.25 kg of 3-hydrazino-5,7-propano-5,6,7,8-tetrahydro-6-pyrido[4,3-c]-pyridazine carboxylic acid ethyl ester fumarate and 3.1 kg of hydroxypropylmethyl cellulose in 16 l of ethanol (96%) and 24 l of water. 16 kg of sugar pellets are sprayed in a fluidized bed apparatus with this suspension. The active substance pellets so produced are sprayed in the same apparatus with a solution of 0.6 kg of ethyl cellulose, 0.3 kg of hydroxypropylmethyl cellulose and 0.12 kg of stearic acid in 14.8 l of methylene chloride and 4.0 l of ethanol (96%). The coated active substance pellets are dried and filled into hard gelatin capsules of capsule size 4.

EXAMPLE 21

10,000 suppositories with an active compound content of 20 mg 20 kg of conventional suppository mass are heated to from 40° to 45° C. 200 g of 3-hydrazino-5,7-propano-5,6,7,8-tetrahydro-6-pyrido[4,3-c]pyridazine carboxylic acid ethyl ester fumarate are stirred into the resulting melt. The obtained suppository mass is homogenized and then poured into molds.

Pharmacology

The substituted pyridazines according to the invention possess valuable pharmacological properties; in particular, they lower the blood pressure, as confirmed by investigations on awake, genetically-hypertensive rats, in which they prove superior to known compounds, such as 3-hydrazino-5,6,7,8-tetrahydro-6-pyrido[4,3-c]pyridazine carboxylic acid ethyl ester, 3-hydrazino-4-methyl-5,6,7,8-tetrahydro-6-pyrido[4,3-c]pyridazine carboxylic acid ethyl ester hydrochloride and hydralazine.

In order to determine the anti-hypertensive effect, the compounds or mixtures are administered once daily by means of an oesophageal sound in the stated doses on two consecutive days to, in each case, 8 rats (Kyoto strain) with genetically-caused hypertension. The blood pressure was measured in each case 6 and 24 hours after administration of the substance.

The measurement of the systolic blood pressure is effected with the aid of an inflatable cuff which is placed around the tail root and on which cuff there are arranged distally annularly 3 piezo-electric crystals (at a distance of 120°) for registering the pulse waves. The determination of the blood pressure is effected through inflation of the cuff and graphic recording of the pulse amplitude [analogously to H. Friebel and E. Vreden, *Arch. exper. Path. u. Pharmakol.*, 232, 419 (1958)]. The animals were kept in an ambience of, and the experiments were carried out at from 22° to 24° C. and from 50 to 60 percent atmospheric humidity. In order to accustom the animals to the measuring process, a measurement was effected on the animals in each case 2 to 3 times daily for three days. For this purpose, as in the subsequent experiments, the rats were put into tunnel-shaped wire cages; one narrow side of the cages is slidable, the other has an opening for taking the tail through. In order to ensure a better blood flow through the tail artery during the measurement, the tails are irradiated for from 5 to 10 minutes with a red light lamp (150 watts) (distance: animal—lamp=50 cm). The air temperature immediately ambient to the tail is from 30° to 33° C. The body of the animals is covered and thus protected from direct irradiation.

The toxicity investigations were carried out on female NMRI mice (body weight from 22 to 26 g). The animals (5 animals per dose) receive food and water ad libitum. Different doses of the substances are administered orally. The duration of observation is 14 days. The $LD_{50}$, i.e. the dose at which 50 percent of the animals die, is determined graphically from the dose effect curve.

In the following Tables, the compounds investigated are characterized by a serial number, which numbers are assigned as follows:

| Serial No. | Name of Compound |
|---|---|
| 1 | 3-hydrazino-5,6,7,8-tetrahydro-6-pyrido[4,3-c]-pyridazine carboxylic acid ethyl ester |
| 2 | 3-hydrazino-4-methyl-5,6,7-8-tetrahydro-6-pyrido-[4,3-c]pyridazine carboxylic acid ethyl ester hydrochloride |
| 3 | hydralazine |
| 4 | 3-hydrazino-5,7-propano-5,6,7,8-tetrahydro-6-pyrido[4,3-c]pyridazine carboxylic acid ethyl ester fumarate |
| 5 | 6-benzoyl-3-isopropylidenehydrazino-5,7-propano-5,6,7,8-tetrahydropyrido[4,3-c]pyridazine |
| 6 | 3-isopropylidenehydrazino-5,7-ethano-5,6,7,8-tetrahydro-6-pyrido[4,3-c]pyridazine carboxylic acid ethyl ester |

Table I reproduces for the representatives of the compounds according to the invention the percentage lowering of the blood pressure after oral administration in the rat and the lethal effect after oral administration in the mouse.

In order to achieve an at least equally effective lowering of blood pressure, e.g. five-fold to ten-fold higher doses (μmole/kg) of hydralazine are needed than of compounds of the Examples 4 to 6. Information on the superior duration of effect of the compounds according to the invention is given by the 24-hour values which, in contrast to the comparison compounds, show, particularly on the second day, a distinctly increased lowering of blood pressure, although the investigations were in part continued with half of the original dose. Moreover, it is to be borne in mind that the compounds according to the invention are three to four times less toxic than hydralazine.

TABLE I

% Change of blood pressure (BP) in genetically-hypertensive rats after single daily application per os on two consecutive days (N = 8/dose) and toxicity (per os; $LD_{50}$) in mice (N = 5/dose)

| Serial | Dose | | BP (% change) 1st day | | 2nd day | | $LD_{50}$ |
|---|---|---|---|---|---|---|---|
| No. | (mg/kg) | (μmole/kg) | 6 h | 24 h | 6 h | 24 h | (mg/kg) |
| 1 | 10 | 42.1 | −24.5 | −6.0 | — | — | 340 |
| 1 | 5 | 21.05 | — | — | −17.5 | 8.5 | |
| 2 | 20 | 79.6 | −4.7 | −1.0 | −4.7 | −3.7 | |
| 3 | 20 | 125.0 | −10.7 | −1.5 | −11.8 | −6.1 | 122* |
| 4 | 2.5 | 9.0 | −9.0 | −11.8 | −15.9 | −17.1 | 400 |
| 5 | 10 | 28.6 | −20.1 | −4.4 | — | — | 510 |
| 5 | 5 | 14.3 | — | — | −15.2 | −12.8 | |
| 6 | 10 | 33.0 | −23.1 | −20.5 | — | — | 300 |

TABLE I-continued

% Change of blood pressure (BP) in genetically-hypertensive rats after single daily application per os on two consecutive days (N = 8/dose) and toxicity (per os; $LD_{50}$) in mice (N = 5/dose)

| Serial | Dose | | BP (% change) 1st day | | 2nd day | | $LD_{50}$ |
|---|---|---|---|---|---|---|---|
| No. | (mg/kg) | (μmole/kg) | 6 h | 24 h | 6 h | 24 h | (mg/kg) |
| 6 | 5 | 16.5 | — | — | −21.5 | −23.1 | |

*L. Dorigotti, R. Rolandi, C. Carpi, Pharmacol. Res. Commun., 8, 295 - 398 (1976)
E. Baldoni, A. Sardi, V. Dezulian, M. Capellini, G. Bianchi, Arzneim. Forschung (Drug Research), 23, 1591 - 95 (1973)

Table II states (for the representatives of the compounds according to the invention) the percentage change of the blood pressure (BP) of genetically-hypertensive rats (24-hour value of the 2nd day) and illustrates the superiority of the compounds according to the invention over the known comparative compounds by means of the calculated therapeutic effectiveness (Th. E.).

TABLE II

Therapeutic effectiveness (Th. E.) calculated from the relation between percentage change of the blood pressure (BP) of genetically-hypertensive rats after 2 days (24-hour value of the 2nd day) and the applied dose (μmole/kg)

| Serial No. | BP (% change) 2nd day, 24 h | Dose (μmole/kg) | Th. E. $\left[\frac{\%\ \text{change BP}}{\mu\text{mole/kg}}\right]$ | Th. E. [Serial No. 3 = 1.0] |
|---|---|---|---|---|
| 1 | −8.5 | 21.05 | 0.404 | 8.3 |
| 2 | −3.7 | 79.6 | 0.046 | 0.9 |
| 3 | −6.1 | 125.0 | 0.0488 | 1.0 |
| 4 | −17.1 | 9.0 | 1.90 | 38.9 |
| 5 | −12.8 | 14.3 | 0.87 | 17.8 |
| 6 | −23.1 | 16.5 | 1.40 | 28.7 |

In Table III there is represented the lowering of the blood pressure of genetically-hypertensive rats in the case of oral application of 3-hydrazino-5,7-propano-5,6,7,8-tetrahydro-6-pyrido[4,3-c]pyridazine carboxylic acid ethyl ester fumarate. In each case 8 animals received the stated dose once daily on 10 consecutive days.

TABLE III

Lowering of the blood pressure of genetically-hypertensive rats (in mm Hg) in the case of administration of different doses of No. 4 (in mg/kg rat), measured on 10 consecutive days (6 hours after application in each case).

| Day | Lowering of the blood pressure (in mm Hg) a | b | c | d |
|---|---|---|---|---|
| 1 | 25.0 | 35.0 | 48.0 | 58.0 |
| 2 | 14.0 | 59.0 | 67.0 | 77.5 |
| 3 | 20.0 | 44.0 | 53.0 | 66.0 |
| 4 | 21.0 | 67.0 | 72.0 | 74.0 |
| 5* | — | — | — | — |
| 6* | — | — | — | — |
| 7 | 27.0 | 53.0 | 59.0 | 69.0 |
| 8 | 21.0 | 66.0 | 67.0 | 66.0 |
| 9 | — | 64.0 | 63.0 | 61.0 |
| 10 | — | 71.0 | 66.0 | 63.0 |

Doses: a = 1.25 mg/kg; b = 2.5 mg/kg; c = 5.0 mg/kg;d = 10.0 mg/kg.
*no measurements Saturday/Sunday The nature and scope of the invention and its advantages are readily understood and appreciated from the preceding description. It is apparent that various changes may be made in the syntheses, in the structure of intermediates, in the acid upon which acid-addition salts are based, in the specific structure of pharmacologically-active and physiologically-acceptable blood-pressure-reducing final products or their therapeutically-acceptable acid-addition salts and/or the precise method of use in accord with which the final products are administered without departing from the spirit and scope of the invention or sacrificing its material advantages. The syntheses, intermediates, acid-addition salts, final products and methods of use hereinbefore described are merely illustrative embodiments of the invention.

What is claimed is:

1. A substituted pyridazine of the formula

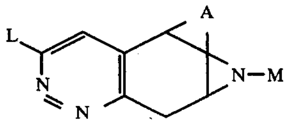

(H)

wherein

A is lower alkylene;

L is —NH—$R^1$ or Z;

M is —H or —C(=X)$R^2$;

$R^1$ is —NH$R^3$, —N($R^4$)$R^5$ or —N=C($R^8$)$R^9$;

$R^2$ is lower alkyl, phen(lower)alkyl, lower alkoxy, lower alkylmercapto, optionally-substituted aryl, phen(lower)alkoxy or —N($R^6$)$R^7$;

$R^3$ is —H, lower alkanoyl, lower alkoxycarbonyl, mono(lower alkyl)carbamoyl or di(lower alkyl)-carbamoyl;

$R^4$ and $R^5$ are, independently, lower alkyl or phen(-lower)alkyl;

$R^6$ and $R^7$ are, independently, —H, lower alkyl, phen(lower)alkyl, optionally-substituted aryl or, taken together and with the nitrogen atom to which both are bound, piperidino, morpholino, piperazino or 4-(lower alkyl)piperazino;

$R^8$ is —H, lower alkyl, phen(lower)alkyl, optionally-substituted aryl or, together with $R^9$, alkylene having from 4 to 11 carbon atoms;

$R^9$ is lower alkyl, phen(lower)alkyl, lower alkenyl, optionally-substituted aryl or, together with $R^8$, alkylene having from 4 to 11 carbon atoms;

X is an oxygen atom or a sulfur atom, and

Z is halo, lower alkoxy or lower alkylmercapto; or an acid-addition salt thereof which is soluble in some solvent;

each aryl having from 6 to 10 ring-carbon atoms;

any substituted aryl being substituted with at most 2 substituents selected from the group consisting of halo, lower alkyl, phen(lower)alkyl, lower alkoxy, lower alkylmercapto, trifluoromethyl or nitro and each "lower" meaning "with from 1 to 5 carbon atoms".

2. A substituted pyridazine according to claim 1 wherein L is Z and M is —C(=X)$R^2$.

3. A substituted pyridazine according to claim 1 wherein L is —NH—$R^1$ and M is —H, or an acid-addition salt thereof.

4. A substituted pyridazine according to claim 1 wherein L is Z and M is —H, or an acid-addition salt thereof.

5. A substituted pyridazine according to claim 1 wherein L is —NH—$R^1$ and M is —C(=X)—$R^2$, or an acid-addition salt thereof.

6. A substituted pyridazine according to claim 1, wherein each "aryl having from 6 to 10 carbon atoms" is phenyl and $R^6$ and $R^7$ are, independently, —H, lower alkyl, phen(lower)alkyl, optionally-substituted phenyl or, taken together and with the nitrogen atom to which both are bound, piperidino, morpholino, piperazino or 4-(lower alkyl)piperazino; or an acid-addition salt thereof.

7. A substituted pyridazine according to claim 5 wherein $R^1$ is —NH$R^3$, $R^2$ is lower alkoxy or phen(-lower)alkoxy and $R^3$ is —H; or an acid-addition salt thereof.

8. A substituted pyridazine according to claim 1 wherein

A is alkylene with 2 or 3 carbon atoms, $R^1$ is —NH—$R^3$ or —N=C($R^8$)$R^9$, $R^2$ is lower alkyl, phen(lower)alkyl, lower alkoxy, optionally-substituted phenyl, phen(lower)alkoxy or —N($R^6$)$R^7$, $R^3$ is —H, lower alkanoyl or lower alkoxycarbonyl, $R^6$ is —H, lower alkyl or, together with $R^7$ and the nitrogen atom to which both are bound, piperidino, morpholino, piperazino or 4-(lower alkyl)-piperazino, $R^7$ is lower alkyl, phen(lower)alkyl, optionally-substituted phenyl or, together with $R^6$ and the nitrogen atom to which both are bound, piperidino, morpholino, piperazino or 4-(lower alkyl)-piperazino, $R^8$ is lower alkyl, phen(lower)alkyl or optionally-substituted phenyl, $R^9$ is lower alkyl, phen(lower)alkyl or optionally-substituted phenyl, X is =O, Z is halo, or an acid-addition salt thereof, any substituted phenyl being substituted with at most 2 substituents selected from the group consisting of halo, lower alkyl, lower alkoxy, trifluoromethyl or nitro and each "lower" meaning "with from 1 to 5 carbon atoms".

9. A physiologically-acceptable substituted pyridazine according to claim 8 wherein L is —NH—$R^1$ and M is —C(=X)—$R^2$, or a therapeutically-acceptable acid-addition salt thereof.

10. A substituted pyridazine according to claim 8 wherein L is Z and M is —C(=X)—$R^2$.

11. A substituted pyridazine according to claim 8 wherein L is —NH—$R^1$ and M is —H, or an acid-addition salt thereof.

12. A substituted pyridazine according to claim 8 wherein L is Z and M is —H, or an acid-addition salt thereof.

13. A substituted pyridazine according to claim 8 wherein:

$R^2$ is lower alkyl, phen(lower)alkyl, lower alkoxy, phenyl, phen(lower)alkoxy or —N($R^6$)$R^7$, $R^3$ is —H or lower alkoxycarbonyl, $R^6$ is —H, $R^7$ is lower alkyl, phen(lower)alkyl or phenyl, $R^8$ is lower alkyl or phen(lower)alkyl, $R^9$ is lower alkyl, phen(lower)alkyl or optionally-monohalosubstituted phenyl and Z is bromo or chloro, or an acid-addition salt thereof, each "lower" meaning "with from 1 to 5 carbon atoms".

14. A physiologically-acceptable substituted pyridazine according to claim 13 wherein L is —NH—$R^1$ and M is —C(=X)—$R^2$, or a therapeutically-acceptable acid-addition salt thereof.

15. A substituted pyridazine according to claim 13 wherein L is Z and M is —C(=X)—$R^2$.

16. A substituted pyridazine according to claim 13 wherein L is —NH—$R^1$ and M is —H, or an acid-addition salt thereof.

17. A substituted pyridazine according to claim 13 wherein L is Z and M is —H, or an acid-addition salt thereof.

18. A substituted pyridazine according to claim 13 wherein $R^3$ is —H or ethoxycarbonyl, $R^7$ is methyl, $R^8$ is methyl or ethyl and $R^9$ is lower alkyl with from 1 to 5 carbon atoms, benzyl or monohalosubstituted phenyl; or an acid-addition salt thereof.

19. A physiologically-acceptable substituted pyridazine according to claim 18 wherein L is —NH—$R^1$ and M is —C(=X)—$R^2$, or a therapeutically-acceptable acid-addition salt thereof.

20. A substituted pyridazine according to claim 18 wherein L is Z and M is —C(=X)—$R^2$, or an acid-addition salt thereof.

21. A substituted pyridazine according to claim 18 wherein L is —NH—$R^1$ and M is —H, or an acid-addition salt thereof.

22. A substituted pyridazine according to claim 18 wherein $R^2$ is tert.-butyl, ethoxy, phenyl or —N($R^6$)$R^7$, $R^8$ is methyl and $R^9$ is methyl, ethyl or p-chlorophenyl; or an acid-addition salt thereof.

23. A physiologically-acceptable substituted pyridazine according to claim 22 wherein L is —NH—$R^1$ and M is —C(=X)—$R^2$, or a therapeutically-acceptable acid-addition salt thereof.

24. A substituted pyridazine according to claim 22 wherein $R^2$ is ethoxy or phenyl, $R^3$ is —H and $R^9$ is methyl; or an acid-addition salt thereof.

25. A physiologically-acceptable substituted pyridazine according to claim 24 wherein L is —NH—$R^1$ and M is —C(=X)—$R^2$, or a therapeutically-acceptable acid-addition salt thereof.

26. A compound according to claim 25 which is 3-hydrazino-5,7-propano-5,6,7,8-tetrahydro-6-pyrido[4,3-c]pyridazine carboxylic acid ethyl ester or a pharmacologically-compatible acid-addition salt thereof.

27. A pharmaceutical composition having therapeutically-acceptable substantially-inert carrier and/or excipient and from 0.5 to 95 percent by weight of a physiologically-acceptable compound according to claim 5, the amount of such compound being from 0.5 to 100 milligrams.

28. An antihypertensive medicament composition comprising carrier and an effective amount of a physiologically-acceptable antihypertensive substituted pyridazine according to claim 5.

29. A process for treating hypertension which comprises administering to a warm-blooded animal afflicted therewith an effective amount of a pharmacologically-active and physiologically-acceptable composition according to claim 28.

* * * * *